US011957462B2

(12) United States Patent
Govari et al.

(10) Patent No.: US 11,957,462 B2
(45) Date of Patent: Apr. 16, 2024

(54) SYSTEM AND METHOD FOR BRAIN CLOT CHARACTERIZATION USING OPTICAL FIBERS HAVING DIFFUSIVE ELEMENTS AND BRAIN CLOT REMOVAL

(71) Applicant: Biosense Webster (Israel) Ltd., Yokneam (IL)

(72) Inventors: Assaf Govari, Haifa (IL); Christopher Thomas Beeckler, Brea, CA (US); Athanassios Papaioannou, Los Angeles, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 329 days.

(21) Appl. No.: 16/548,153

(22) Filed: Aug. 22, 2019

(65) Prior Publication Data

US 2021/0052201 A1 Feb. 25, 2021

(51) Int. Cl.
*A61B 5/1459* (2006.01)
*A61B 5/00* (2006.01)
(Continued)

(52) U.S. Cl.
CPC .......... *A61B 5/1459* (2013.01); *A61B 5/0036* (2018.08); *A61B 5/0037* (2013.01);
(Continued)

(58) Field of Classification Search
CPC .... A61B 2034/2051; A61B 2034/2072; A61B 2090/306; A61B 2090/376;
(Continued)

(56) References Cited

U.S. PATENT DOCUMENTS 5,166,990 A * 11/1992 Riccitelli ........... A61B 5/14539
385/12
5,625,459 A 4/1997 Driver
(Continued)

FOREIGN PATENT DOCUMENTS

WO 03051184 A1 6/2006
WO WO-2016168605 A1 * 10/2016 ........... A61B 5/0084
(Continued)

OTHER PUBLICATIONS

Joe Zhou et al., "Optical Fiber Tips and Their Applications," Nov. 2007, Polymicro Technologies, pp. 1-5 (Year: 2007).*
(Continued)

*Primary Examiner* — Joseph M Santos Rodriguez
*Assistant Examiner* — Maria Christina Talty
(74) *Attorney, Agent, or Firm* — Troutman Pepper Hamilton Sanders LLP

(57) ABSTRACT

A medical system includes a probe, an electro-optical measurement unit, and a processor. The probe is configured for insertion into a blood vessel of a brain, and includes two optical fibers, which include each an optical diffuser at distal ends thereof. One fiber is configured to guide an optical signal to a location along the blood vessel and to diffuse the optical signal so as to interact with a brain clot in the blood vessel. The other fiber is configured to collect the diffused optical signal that interacted with the brain clot at another location along the blood vessel. The electro-optical measurement unit is configured to transmit the optical signal to one optical fiber, and to receive and measure the diffused optical signal from the other optical fiber. The processor is configured to identify a composition of the brain clot by analyzing the measured diffused optical signal.

14 Claims, 3 Drawing Sheets

(51) Int. Cl.
*A61B 5/06* (2006.01)
*A61B 90/00* (2016.01)

(52) U.S. Cl.
CPC .......... *A61B 5/0042* (2013.01); *A61B 5/062* (2013.01); *A61B 5/6868* (2013.01); *A61B 90/39* (2016.02); *A61B 2090/3966* (2016.02)

(58) Field of Classification Search
CPC .... A61B 2090/3762; A61B 2090/3966; A61B 2562/0233; A61B 2562/04; A61B 34/20; A61B 5/0036; A61B 5/0037; A61B 5/0042; A61B 5/0086; A61B 5/02007; A61B 5/062; A61B 5/064; A61B 5/1459; A61B 5/6852; A61B 5/6868; A61B 5/6876; A61B 90/39; G01N 2021/4742; G01N 2201/0634; G02B 6/00
See application file for complete search history.

(56) References Cited

U.S. PATENT DOCUMENTS

| | | | | |
|---|---|---|---|---|
| 5,664,574 | A | 9/1997 | Chance | |
| 5,953,477 | A | 9/1999 | Wach et al. | |
| 7,194,296 | B2 * | 3/2007 | Frantz | A61B 5/06 324/207.13 |
| 8,029,766 | B2 | 10/2011 | Elmaleh et al. | |
| RE43,750 | E * | 10/2012 | Martinelli | A61B 34/20 128/899 |
| 2004/0111016 | A1 * | 6/2004 | Casscells, III | A61B 5/1459 356/300 |
| 2007/0123776 | A1 * | 5/2007 | Aharoni | A61B 5/1076 600/437 |
| 2007/0167743 | A1 * | 7/2007 | Honda | A61B 5/6831 600/424 |
| 2008/0300493 | A1 * | 12/2008 | Gatto | A61B 90/36 600/479 |
| 2010/0234793 | A1 | 9/2010 | Dacey et al. | |
| 2010/0286531 | A1 * | 11/2010 | Ryan | A61B 5/0066 600/478 |
| 2014/0180056 | A1 * | 6/2014 | Hoseit | A61B 5/6852 600/407 |
| 2014/0276684 | A1 * | 9/2014 | Huennekens | A61B 17/320758 606/7 |
| 2015/0057646 | A1 * | 2/2015 | Aljuri | A61B 1/307 606/10 |
| 2016/0022146 | A1 * | 1/2016 | Piron | A61B 8/445 600/411 |
| 2018/0085130 | A1 * | 3/2018 | Fung | A61B 17/12122 |
| 2018/0125372 | A1 * | 5/2018 | Petroff | A61B 5/6852 |
| 2019/0021646 | A1 * | 1/2019 | Bannon | A61B 5/7246 |
| 2019/0274528 | A1 * | 9/2019 | Petroff | A61B 17/00234 |
| 2019/0365248 | A1 * | 12/2019 | Mueller | A61B 5/0075 |
| 2019/0388002 | A1 * | 12/2019 | Bozsak | G16B 40/20 |

FOREIGN PATENT DOCUMENTS

| | | | | |
|---|---|---|---|---|
| WO | WO-2017216645 A2 * | 12/2017 | .......... | A61B 5/0036 |
| WO | WO-2018137949 A1 * | 8/2018 | .......... | A61B 5/0075 |

OTHER PUBLICATIONS

Pinnacle Biologics, "Optiguide Fiber Optic," 2014, pp. 1-2 (Year: 2014).*

R. Nogueira et al., "The Trevo device: preclinical data of a novel stroke thrombectomy device in two different animal models of arterial thrombo-occlusive disease," 2012, Jounral of NeuroIntervnetional Surgery, 4, pp. 295-300. (Year: 2012).*

Pending U.S. Appl. No. 16/057,189, filed Aug. 7, 2018, entitled "Brain Clot Characterization Using Optical Signal Analysis, and Corresponding Stent Selection".

Pending U.S. Appl. No. 16/192,156, filed Nov. 15, 2018, entitled "Catheter with Irrigator and/or Aspirator and with Fiberoptic brain-clot Analyzer".

Pending U.S. Appl. No. 15/674,380, filed Aug. 10, 2017, entitled "ENT Image Registration".

U.S. Appl. No. 62/675,952, filed May 24, 2018, entitled "Position Sensor on Brain-Clot Removal Sheath and Location Pad Collar".

Pending U.S. Appl. No. 16/248,393, filed Jan. 15, 2019, entitled "Position Sensor on Brain-Clot Removal Sheath and Location Pad Collar".

European Search Report for Application No. 20192083.2-1132, dated Apr. 8, 2021.

* cited by examiner

SYSTEM AND METHOD FOR BRAIN CLOT CHARACTERIZATION USING OPTICAL FIBERS HAVING DIFFUSIVE ELEMENTS AND BRAIN CLOT REMOVAL

FIELD OF THE INVENTION

The present invention relates generally to invasive medical probes, and particularly to catheters for cerebrovascular applications.

BACKGROUND OF THE INVENTION

Various types of medical probes include optical elements. For example, U.S. Patent Application Publication 2008/0300493 describes devices and related methods for detecting blood clots in a blood vessel. An optical microprobe is configured to illuminate a blood vessel with electromagnetic radiation corresponding to the near-infrared portion of the electromagnetic spectrum. The optical microprobe has a pair of fiber optic strands configured for transmission spectroscopy to obtain the absorption spectrum generated by the components within the blood vessel. Correspondingly, the distal ends of the fiber optic strands are positioned in a diametrically opposed configuration. Because blood clots generate a detectable and unique spectrum, the presence or absence of the blood clot is determined by examining the blood vessel absorption spectrum. A specially-designed holder is configured to stably position the optical microprobe relative to the blood vessel and is used to facilitate precise blood clot detection along a length of blood vessel.

As another example, U.S. Patent Application Publication 2016/0022146 describes insertable imaging devices and methods of use thereof in minimally invasive medical procedures. In some embodiments, the imaging device is integrated into an access port, thereby allowing imaging of internal tissues within the vicinity of the access port, while, for example, enabling manipulation of surgical tools in the surgical field of interest. In other embodiments, the imaging devices is integrated into an imaging sleeve that is insertable into an access port. The imaging method may be based on, but are not limited to, optical imaging such as hyperspectral imaging and optical coherence tomography. In an embodiment, optical diffusers can be utilized at the distal end of optical fibers or light guides to provide directionally homogenized illumination light.

U.S. Pat. No. 8,029,766 describes a probe-type imaging device useful to visualize interior surfaces, e.g., the lumen of blood vessels. Specifically, the probe-type device is particularly useful for direct tissue imaging in the presence or absence of molecular imaging agents. In one embodiment, light diffusers may be used to deliver illumination light of appropriate frequency from the catheter to the vessel wall.

SUMMARY OF THE INVENTION

There is provided, in accordance with an embodiment of the present invention, a medical system including a probe, an electro-optical measurement unit, and a processor. The probe is configured for insertion into a blood vessel of a brain, and includes (a) a first optical fiber, which includes a first optical diffuser at a distal end thereof and which is configured to guide an optical signal to a first location along the blood vessel and to diffuse the optical signal so as to interact with a brain clot in the blood vessel, and (b) a second optical fiber, which includes a second optical diffuser at a distal end thereof and which is configured to collect the diffused optical signal that interacted with the brain clot, at a second location along the blood vessel that is different from the first location. The electro-optical measurement unit is configured to transmit the optical signal to the first optical fiber, and to receive and measure the diffused optical signal from the second optical fiber. The processor is configured to identify a composition of the brain clot by analyzing the measured diffused optical signal.

In some embodiments, the processor is further configured to output a recommendation for selecting a brain-clot removal method that matches the composition of the brain clot.

In some embodiments, the processor is configured to analyze the measured diffused optical signal by distinguishing between an absorption-related component and a scattering-related component in the diffused optical signal.

In an embodiment, the first location of the first optical diffuser is more distal than the second location of the second optical diffuser. In another embodiment, the first location of the first optical diffuser is more proximal than the second location of the second optical diffuser.

In some embodiments, the probe further includes a working channel. In other embodiments, the probe further includes radiopaque markers.

There is additionally provided, in accordance with an embodiment of the present invention, a method including inserting a probe into a blood vessel of a brain, the probe including (a) a first optical fiber, which includes a first optical diffuser at a distal end thereof and which is configured to guide an optical signal to a first location along the blood vessel and to diffuse the optical signal so as to interact with a brain clot in the blood vessel, and (b) a second optical fiber, which includes a second optical diffuser at a distal end thereof and which is configured to collect the diffused optical signal that interacted with the brain clot, at a second location along the blood vessel that is different from the first location.

The optical signal is transmitted to the first optical fiber, and the diffused optical signal is received from the second optical fiber and measured. A composition of the brain clot is identified by analyzing the measured diffused optical signal.

In some embodiments, the method further includes eliminating the clot based on the identified composition.

There is additionally provided, in accordance with an embodiment of the present invention, a medical probe for insertion into a blood vessel of a brain, the probe including (a) a first optical fiber, which includes a first optical diffuser at a distal end thereof and which is configured to guide an optical signal to a first location along the blood vessel and to diffuse the optical signal so as to interact with a brain clot in the blood vessel, and (b) a second optical fiber, which includes a second optical diffuser at a distal end thereof and which is configured to collect the diffused optical signal that interacted with the brain clot, at a second location along the blood vessel that is different from the first location.

The present invention will be more fully understood from the following detailed description of the embodiments thereof, taken together with the drawings in which:

DETAILED DESCRIPTION OF EMBODIMENTS

Overview

Figure 1A:
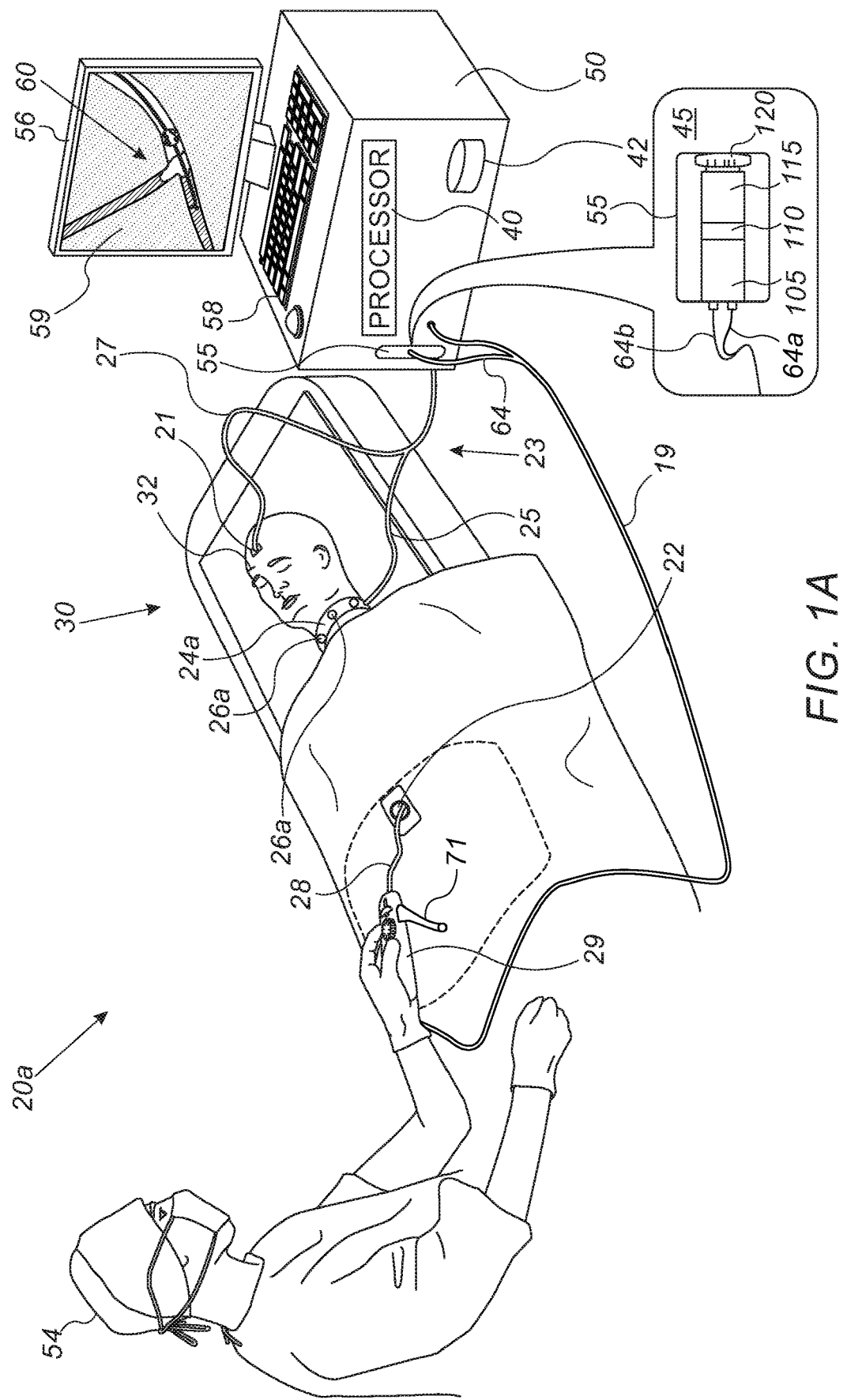
FIGS. 1A and 1B are schematic, pictorial illustrations of catheter-based clot composition analysis and removal systems, in accordance with embodiments of the present invention.

An ischemic stroke, typically caused by an obstructing clot in a large blood vessel of the brain, is an emergency medical condition. Clot composition may vary, for example, from a preponderance of fibrin, typically making the clot relatively solid and hard, to a preponderance of red blood cells, which typically form a relatively gel-like and pliable clot. This diverse composition of clot influences several of its properties, including the optical and mechanical ones. Successful elimination of a clot may depend on selecting a technique that is most suitable for engaging a specific clot composition. Therefore, it is important to analyze clot composition before attempting its removal.

A non-diffusive fiber-optic based system and method for the analysis and identification of the composition of a brain clot to indicate clot characteristics is described in U.S. patent application Ser. No. 16/057,189, filed Aug. 7, 2018, entitled "Brain Clot Characterization Using Optical Signal Analysis, and Corresponding Stent Selection," which is assigned to the assignee of the present patent application and whose disclosure is incorporated herein by reference. The term "composition of a clot" refers therein to various chemical, biological and/or physical characteristics of the clot and/or the elements making-up the clot.

Embodiments of the present invention that are described hereinafter provide an optical diffusive signal-based system and method for enhancing the measurement and analysis of the composition of a brain clot in a 3D region surrounding the fiber optic. In some embodiments, a probe comprises two optical channels, such as optical fibers (also referred to as fiber optics—FO), having respective optical diffusing elements processed or added to their distal ends. One fiber emits diffusive light and the other fiber collects and guides the diffusive light after the diffusive light interacts with the clot composition.

The two diffusers are staggered, i.e., they are not next to each other, as described below. The staggered diffusers may (a) enable a signal analysis unit to differentiate between absorption and scattering properties of the clot composition, and thus add more information regarding the clot composition, and (b) obtain signals from an increased 3D region of the surrounding the FO ends, so that the signal may more effectively represent a bulk composition of the clot. The use of the staggered diffusers may therefore increase the sensitivity and specificity of a fiber-optic based system and method for the analysis and identification of the composition of a brain clot.

It should be understood that by referring to two optical channels, e.g., two fibers, the disclosed description covers the use of more than two fibers; i.e., using a first plurality of illuminating fibers and a second plurality of collecting fibers (not necessarily equal in number to the illuminating fibers), with all fibers incorporating diffusive elements. Each plurality of fibers may be arranged in various staggered configurations relative to the distal end of the probe.

In some embodiments the optical signal is emitted by the more distal diffuser and fiber, and collected by the more proximal diffuser and fiber. In alternative embodiments the roles of the fibers may be switched, i.e., the optical signal is emitted by the more proximal diffuser and fiber, and collected by the more distal diffuser and fiber.

The optical fibers are coupled at their proximal ends to an electro-optical measurement unit, which collects and measures the diffused optical signal that interacts with the clot, and the output of one of the fibers. The unit digitizes the measured signal, and outputs the digital signal to a processor which analyzes the digital signal to identify the composition of the clot. In some embodiments, the processor is further configured to output a recommendation for selecting a brain clot removal technique that matches the identified composition of the brain clot.

In an embodiment, a medical system is provided, which comprises a probe for insertion into a blood vessel of a brain, the probe comprising (a) a first optical fiber, which comprises a first optical diffuser at a distal end thereof and which is configured to guide an optical signal to a first location along the blood vessel and to diffuse the optical signal so as to interact with a brain clot in the blood vessel, and (b) a second optical fiber, which comprises a second optical diffuser at a distal end thereof and which is configured to collect the diffused optical signal that interacted with the brain clot, at a second location along the blood vessel that is different from the first location. The medical system further comprises (i) an electro-optical measurement unit, configured to transmit the optical signal to the first optical fiber, and to receive and measure the diffused optical signal from the second optical fiber, and (ii) a processor, configured to identify a composition of the brain clot by analyzing the measured diffused optical signal.

Typically, the processor is programmed in software containing a particular algorithm that enables the processor to conduct each of the processor-related steps and functions outlined above.

The disclosed probe further comprises one or more working channels that can be (i) coupled to an irrigation/aspiration treatment unit, configured to dissolve the clot by irrigation, and/or remove it by suction aspiration, and/or (ii) be used to advance a clot removal device, such as a stentriever, to be inserted into the blood vessel to retract the clot.

By using a volumetric diffusive light signal, the disclosed system and method for analyzing clot composition may improve the clinical outcome of a medical emergency catheterization procedure for the removal of a brain clot by allowing the physician to select a device tailored to remove a certain type of clot.

System Description

Figure 1B:
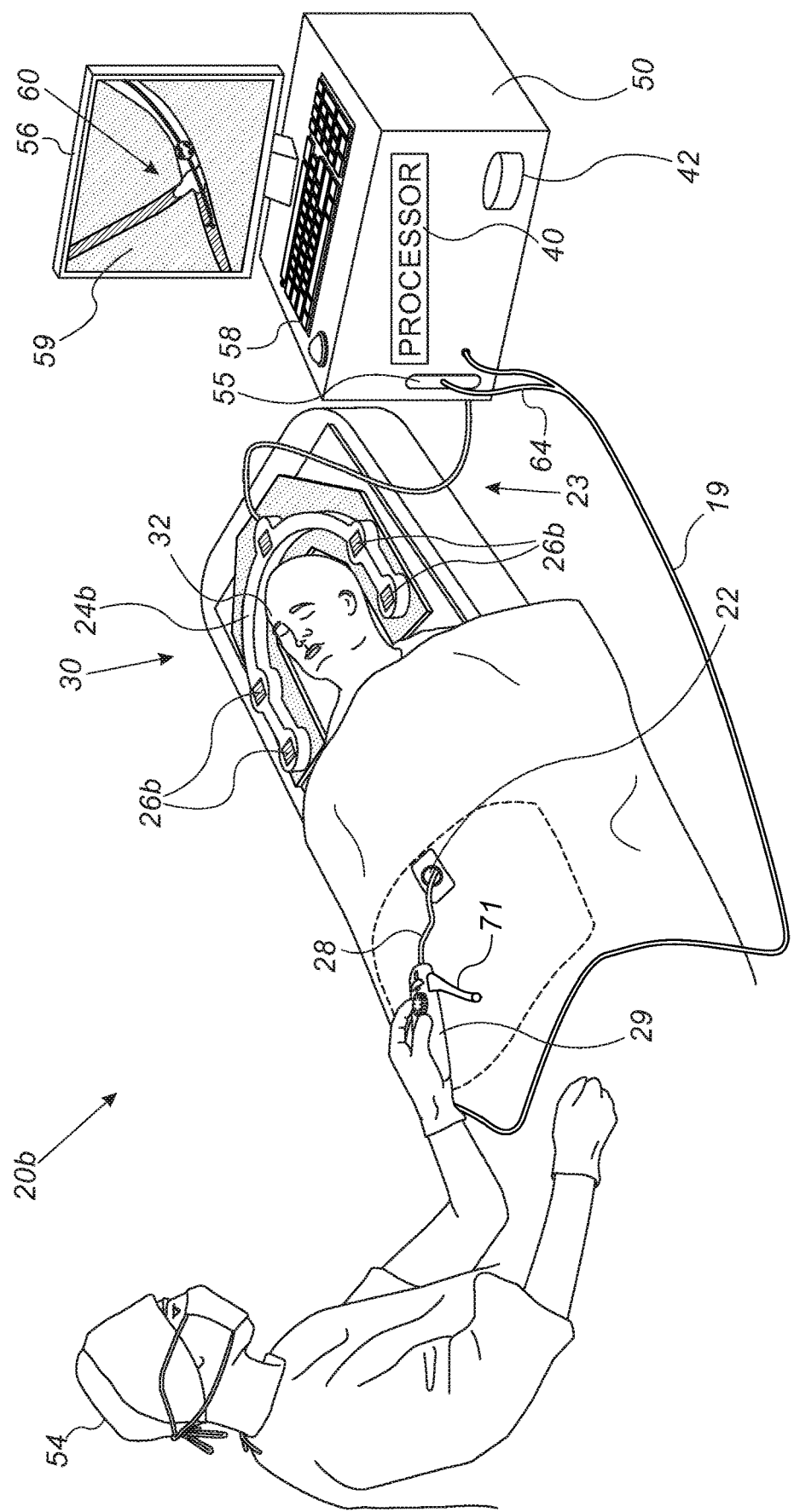

FIGS. 1A and 1B are schematic, pictorial illustrations of catheter-based clot composition analysis and removal systems 20a and 20b, in accordance with embodiments of the present invention.

In some embodiments, prior to performing the catherization procedure, CT images of a patient 22 are acquired. The CT images are stored in a memory 42 for subsequent retrieval by a processor 40. The processor uses the images to present, for example, brain section image 59 demonstrating a clot on a display 56. In another embodiment, during the disclosed catheterization, procedure systems 20a and 20b register a position of a distal end of a catheter 28 inside the patient's brain, with frames of reference of brain images of patient 32, herein assumed, by way of example, to comprise real-time fluoroscopic images. The position of a catheter distal end is tracked using a magnetic tracking sub-system 23, which tracks spatial coordinates of a magnetic sensor fitted at the distal end.

Using magnetic position tracking sub-system 23, a physician 54 advances the distal end of catheter 28 through blood vessels, usually arteries, to the clot so as to enable diagnosis of the type of clot and optionally to perform a corresponding therapeutic procedure to remove the clot. In some embodiments of the present invention, a working channel 71 is included in catheter 28, through which a clot removal device, such as a clot removing stent, a stentriever, can be inserted. Alternatively or additionally, a system, such as an irrigation/aspiration clot removal system, can be coupled to working channel 71. An irrigation/aspiration clot removal system is described in U.S. patent application Ser. No. 16/192,156, filed Nov. 15, 2018, entitled "Catheter with Irrigator and/or Aspirator and with Fiberoptic brain-clot Analyzer," which is assigned to the assignee of the present patent application and whose disclosure is incorporated herein by reference.

In system 20a, shown in FIG. 1A, a location pad 24a, comprised of magnetic tracking sub-system 23, is implemented as a collar put around the neck of patient 32. By putting location pad 24a over the neck, location pad 24a is configured to automatically compensate for patient head movement. Location pad 24a comprises magnetic field radiators 26a which are fixed in position relative to the head of patient 32 and which transmit alternating sinusoidal magnetic fields into a region 30 where the head of patient 32 is located. A console 50 electrically drives radiators 26a via a cable 25. In an embodiment, further compensation of head motion is provided by attaching a reference sensor 21 to the patient's forehead. Console 50 is configured to receive signals from reference sensor 21 via a cable 27. A location tracking system that comprises a neck collar location pad is described in the aforementioned U.S. patent application Ser. No. 16/057,189.

Physician 54, operating system 20a, holds catheter controller handle 29, which is connected to the proximal end of catheter 28. Controller 29 allows the physician to advance and navigate catheter 28 in the brain, for example, through an entry point 22 at an artery at a thigh of patient 32. As noted above and described below, physician 54 navigates the distal end of catheter 28 using position signals from a magnetic position sensor fitted at the distal end of catheter 28. Console 50 receives the position signals via a cable 19 that connects to catheter 28 via handle 29.

Elements of system 20a, including radiators 26a, are controlled by a system processor 40, comprising a processing unit communicating with one or more memories. Processor 40 may be mounted in console 50, which comprises operating controls 58 that typically include a keypad and/or a pointing device such as a mouse or trackball. Physician 54 uses operating controls on handle 29 to interact with the processor while performing the registration of system 20a. During the registration process, an image 59 of a brain section is presented on display 56. Subsequent to the registration process described above, physician 54 uses the operating controls to advance the distal end of catheter 28 to a brain location where a clot is blocking an artery. The processor presents results of the catheter tracking procedure on display 56.

Processor 40 uses software stored in a memory 42 to operate system 20a. The software may be downloaded to processor 40 in electronic form, over a network, for example, or it may, alternatively or additionally, be provided and/or stored on non-transitory tangible media, such as magnetic, optical, or electronic memory. In particular, processor 40 runs a dedicated algorithm as disclosed herein, included in FIG. 3, that enables processor 40 to perform the disclosed steps, as further described below.

In some embodiments of the present invention, an electro-optical measurement unit 55 is included in console 50. Electro-optical measurement unit 55 is configured to collect, using a fiber optic 64b, a diffusive optical signal output from a fiber optic 64a, both of which are included in catheter 28 (collectively marked also as optical fibers 64). The two FOs run in cable 19 to console 50. Electro-optical measurement unit 55 measures the collected signal and conveys the measured signal to processor 40. Based on the measured signal analysis, processor 40 identifies the composition of a clot, as further elaborated below. In some embodiments, the processor presents the identified clot composition on display 56.

In some embodiments, as seen in inset 45, electro-optical measurement unit 55 comprises an optical coupler 105, which may include either a monochromatic or wideband light source (not shown), such as an incandescent lamp, LED, or a laser-diode. For example, such a source may illuminate the clot with monochromatic red light or with white light. For clot illumination, coupler 105 couples the light source into a proximal edge of optical fiber 64a. Coupler 105 is further configured to couple, to a detector 110, an optical signal output of fiber 64b (i.e., diffused light that interacts with the clot). Detector 110 converts the coupled output optical signal into an electrical analog signal. An analog-to-digital conversion circuit 115 digitizes the analog signal and a connector 120 conveys the digitized signal to processor 40 for analysis. In an embodiment, connector 120 is further configured to connect electro-optical measurement unit 55 to an electrical supply.

System 20b, shown in FIG. 1B, has a different magnetic location pad design, namely a location pad 24b. As seen, location pad 24b is fixed to the bed, and irradiators 26b surround a patient headrest horizontally. In this example, system 20b lacks reference sensor 21, and therefore the head of the patient must be fixated to keep it motionless. In general, other components of system 20b are identical to those of system 20a. A location tracking system using a location pad similar to location pad 24b is described in U.S. patent application Ser. No. 15/674,380, filed Aug. 10, 2017, entitled "ENT Image Registration," which is assigned to the assignee of the present patent application and whose disclosure is incorporated herein by reference.

Systems 20a and 20b shown in FIGS. 1A and 1B are chosen purely for the sake of conceptual clarity. Other system elements may be included, for example additional controls on handle 29 for controlling the diagnostic tooling designed to determine clot type. CARTO® magnetic tracking systems, which track a location and orientation of a magnetic position sensor in an organ of a body using techniques similar to those applied by systems 20a and 20b, are produced by Biosense-Webster, Irvine, California.

Brain Clot Characterization Using Optical Fibers Having Diffusive Elements

Figure 2:
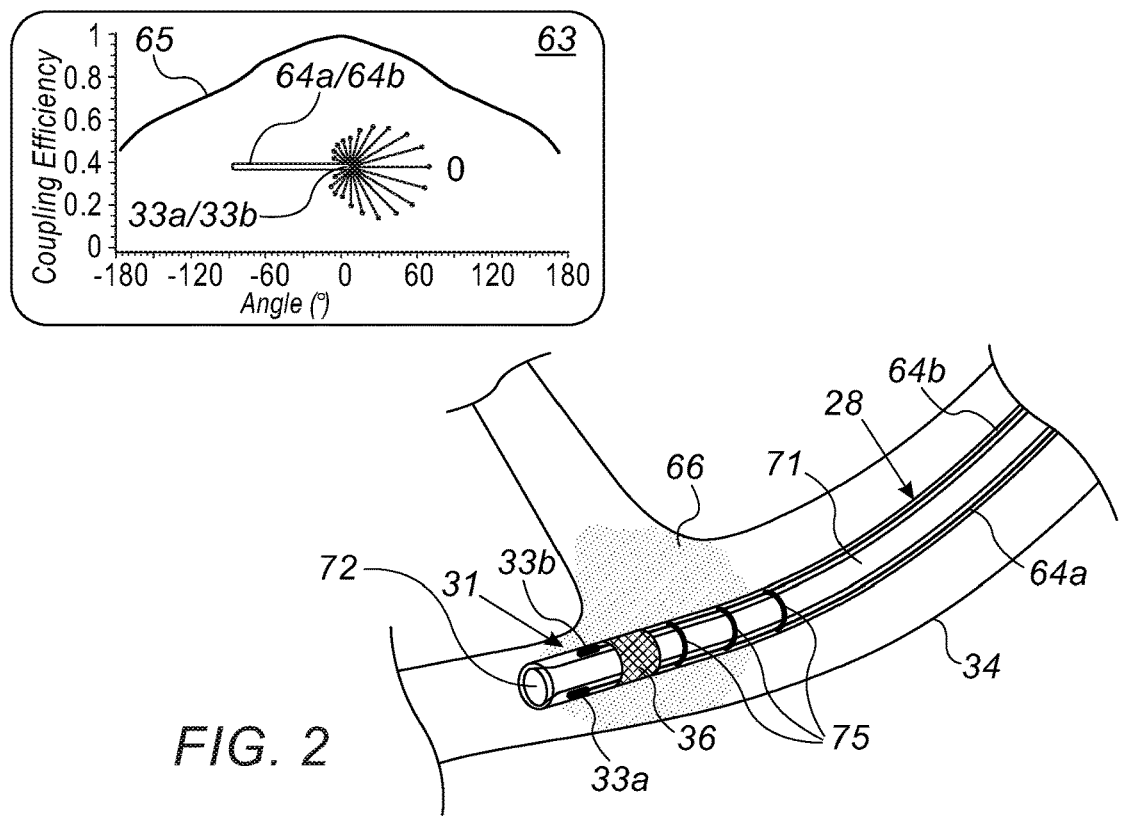
FIG. 2 is a schematic cross-sectional view of a brain clot and a catheter, in accordance with an embodiment of the present invention.

FIG. 2 is a schematic cross-sectional view of a brain clot 66 and a catheter 28, in accordance with an embodiment of the present invention. As seen, clot 66 blocks blood flow in an artery 34, where, in some embodiments, physician 54 navigates and advances catheter 28 distally in artery 34, to a location beyond clot 66.

A distal end 31 of catheter 28 comprises a magnetic position sensor 36, which is used for tracking distal end 31 in the brain to assist in navigating distal end 31 to clot 66. A system and method for tracking catheter 28 and have it to engage (e.g., penetrate or traverse) clot 66 are described in U.S. Provisional Patent Application 62/675,952, filed May 24, 2018, entitled "POSITION SENSOR ON BRAIN-CLOT REMOVAL SHEATH AND LOCATION PAD COLLAR" and U.S. patent application Ser. No. 16/248,393, filed Jan. 15, 2019, entitled "POSITION SENSOR ON BRAIN-CLOT REMOVAL SHEATH AND LOCATION PAD COLLAR," which are assigned to the assignee of the present patent application and whose disclosures are incorporated herein by reference.

Catheter 28 comprises optical fibers 64a and 64b to guide an optical signal. In an embodiment, electro-optical measurement unit 55 (shown in FIGS. 1A and 1B) couples the proximal edge of a fiber 64a to illuminate clot 66 via a diffuser 33a, and collects, via diffuser 33b and fiber 64b, a resulting diagnostic optical signal to analyze the signal. Diffusers 33a and 33b can be produced by various methods, such as but not limited to, tapering the optical fiber into a tip, surface roughening the fiber, and/or by coupling a diffuser element to a distal portion of the optical fiber, including coupling a diffuser element at the distal emitting/receiving edge of the fiber.

Unit 55 further conveys the analyzed signal to processor 40. The processor analyzes the conveyed measured signals to identify the composition of clot 66. A system and method for brain clot 66 characterization using optical signal analysis are described in the above cited U.S. patent application Ser. No. 16/057,189.

As seen in FIG. 2, diffusers 33a and 33b are staggered, i.e., they are not next to each other, which allows the system to differentiate between absorption and scattering properties of clot 66, as described below. An inset 63 shows schematically the coupling efficiency 65 to clot 66 as a function of angle of a diffuser such as diffusers 33a and 33b, for either transmitting or receiving an optical wave. As seen, coupling efficiency 65 is broad and covers practically all detections of incidents of an optical wave.

The staggering and addition of diffusers may enable signal analysis unit 55 and processor 40 to differentiate between clot composition absorption, represented in Eq. 1 below by $\mu_a$, and composition scattering properties, represented by $\mu_s$ in Eq. 1 below. In an embodiment, processor 40 distinguishes between the absorption component and the scattering component of a given received signal by solving Eq. 1 with a best fit for $\mu_a$ and $\mu_s$.

$$\frac{\partial \Psi(r,t)}{\partial t} = D\nabla^2 \Psi(r,t) - \frac{c}{n}\mu_a \Psi(r,t) + \frac{c}{n}S(r,t), \quad \text{Eq. 1}$$

where $\Psi(r,t)$ is photon fluence rate, S is a light source term, c/n is speed of light in the clot, $\mu_a$ is absorption coefficient of light taking a direct linear trajectory between diffusers 33a and 33b, and $$D = \frac{c}{3n\mu_s l}$$

is photon diffusion coefficient with $\mu_s$ being scattering coefficients and l the mean free path of a scattered photon in clot 66 between diffusers 33a and 33b.

In some cases, using a pulsed light source S(r,t) may result in measurable inelastic photon scattering that produces signals at wavelengths different than those outputted, which may further enhance the indicative power of the disclosed optical technique.

In some embodiments, catheter 28 comprises a working channel 71 having a channel opening 72. Channel 71 may be coupled to a treatment unit that is used for dissolving and/or aspiration removal of the clot, if a clot composition measurement and analysis, as described above, confirms that the above-mentioned means are suitable to treat the identified clot. In the event that the optical measurement and subsequent analysis indicates otherwise, for example, that the clot is too dense for aspiration, a different tool may be inserted via working channel 71 into clotted blood vessel 34, such as a stentriever (not shown).

Finally, catheter 28 comprises radiopaque markers 75 for tracking its distal end using X-ray based imaging modalities such as fluoroscopy (e.g., using a C-arm) and/or CT.

The example illustration shown in FIG. 2 is chosen purely for the sake of conceptual clarity. For example, in another embodiment, diffusers 33a and 33b may be located proximally to the distal edge of the optical fibers and/or staggered differently.

Figure 3:
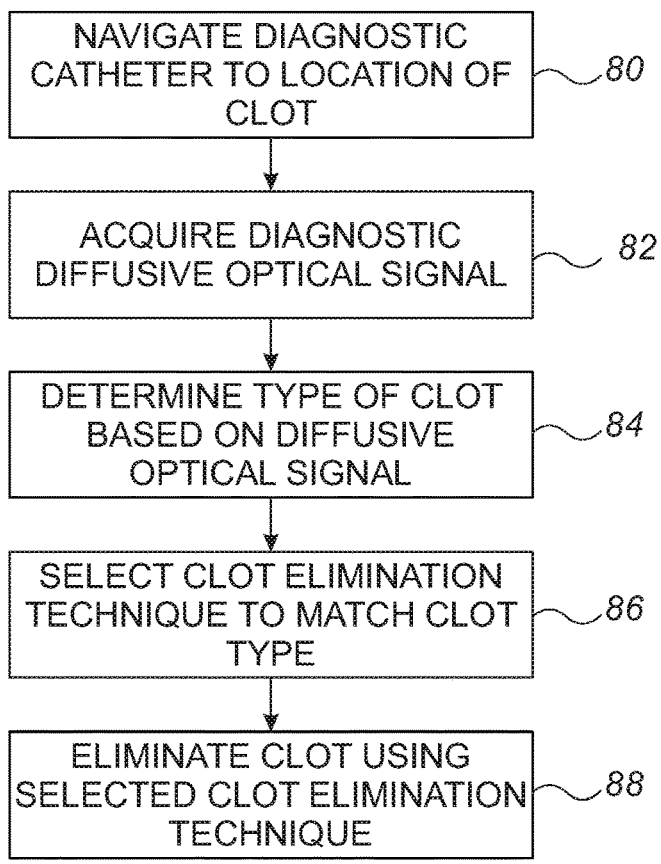
FIG. 3 is a flow chart that schematically illustrates a method for clot composition analysis using diffusive light, and subsequent selection of clot removal method, in accordance with an embodiment of the present invention.

FIG. 3 is a flow chart that schematically illustrates a method for clot composition analysis, and subsequent selection of clot removal method, in accordance with an embodiment of the present invention. The process begins with physician 54 navigating catheter 28 to traverse clot 66 with the catheter distal end, at a navigation step 80. Next, physician 54 operates an optical sensing system, comprising optical transmitting/receiving diffusers 33a and 33b in catheter 28, to measure a diffusive optical signal indicative of clot 66 composition, at a signal acquisition step 82.

Next, processor 40 analyzes the measured signals, so as to identify the composition of clot 66 (i.e., type of clot), at a clot analysis step 84.

Next, based on the identified composition of clot 66, which processor 40 may present to physician 54 on display 56, physician 54 selects an appropriate clot elimination technique for eliminating clot 66 from the brain of patient 32, at an elimination technique selection step 86. In some embodiments, physician 54 selects to dissolve and/or aspire, or using a stentriever, remove clot 66. Finally, physician 54 eliminates clot 66 using the selected brain clot elimination technique, at a clot elimination step 88.

The example flow chart shown in FIG. 3 is chosen purely for the sake of conceptual clarity. In alternative embodiments, for example, based on the indication from processor 40, physician 54 may choose to remove the clot by another clot removal device inserted through working channel 71.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A medical system, comprising:
   a probe for insertion into a blood vessel of a brain, the probe comprising:
      a first optical fiber, which comprises a first optical diffuser at a distal end thereof and which is configured to guide an optical signal to a first location in and along the blood vessel and to diffuse the optical signal so as to interact with a brain clot in the blood vessel;
      a second optical fiber, which comprises a second optical diffuser at a distal end thereof and longitudinally staggered relative to the first optical diffuser and which is configured to collect the diffused optical signal that interacted with the brain clot, at a second location in and along the blood vessel that is different from the first location;
      a lumen extending along the probe and defining a working channel, the working channel configured to receive, and for removal of, the brain clot; and
      a magnetic position sensor configured to detect a magnetic field output by a magnetic field radiator; and
   an electro-optical measurement unit comprising an optical coupler and a light source, the electro-optical measurement unit configured to transmit the optical signal to the first optical fiber, and to receive and measure the diffused optical signal from the second optical fiber; and
   a processor, configured to:
      identify a composition of the brain clot by analyzing the measured diffused optical signal, wherein analyzing the measured diffused optical signal comprises distinguishing between an absorption-related component and a scattering-related component in the measured diffused optical signal;
      determine a position and orientation of the probe based at least in part on signals received from the magnetic position sensor;
      output to a connected display an image representative of the brain clot and a position and orientation of the probe;
      output to the connected display the identified composition of the brain clot; and
      output to the connected display a recommendation for selecting a brain clot removal technique using a method that matches the composition of the brain clot and includes removal of the brain clot via the working channel.

2. The medical system according to claim 1, wherein the first location of the first optical diffuser is more distal than the second location of the second optical diffuser.

3. The medical system according to claim 1, wherein the first location of the first optical diffuser is more proximal than the second location of the second optical diffuser.

4. The medical system according to claim 1, wherein the probe further comprises radiopaque markers.

5. The medical system according to claim 1, further comprising a magnetic field subsystem comprising a collar configured for placement around a neck of a patient, the collar comprising the magnetic field radiator.

6. The medical system according to claim 5, the magnetic field subsystem further comprising a reference sensor configured for attachment to a forehead of the patient.

7. The medical system according to claim 1, further comprising a magnetic field subsystem comprising a location pad fixed to a bed, the location pad comprising the magnetic field radiator.

8. The medical system according to claim 1, the working channel being configured for aspiration removal of a clot.

9. The medical system according to claim 1, the working channel being configured for insertion of a stentriever.

10. A medical method, comprising:
    inserting a probe into a blood vessel of a brain, the probe comprising:
       a first optical fiber, which comprises a first optical diffuser at a distal end thereof and which is configured to guide an optical signal to a first location in and along the blood vessel and to diffuse the optical signal so as to interact with a brain clot in the blood vessel;
       a second optical fiber, which comprises a second optical diffuser at a distal end thereof and longitudinally staggered relative to the first optical diffuser and which is configured to collect the diffused optical signal that interacted with the brain clot, at a second location in and along the blood vessel that is different from the first location;
       a lumen extending along the probe and defining a working channel, the working channel configured to receive, and for removal of, the brain clot; and
       a magnetic position sensor configured to detect a magnetic field output by a magnetic field radiator;
    determining a position and orientation of the probe based at least in part on signals received from the magnetic position sensor;
    transmitting the optical signal to the first optical fiber, and receiving and measuring the diffused optical signal from the second optical fiber; and
    identifying a composition of the brain clot by analyzing the measured diffused optical signal, wherein analyzing the measured diffused optical signal comprises distinguishing between an absorption-related component and a scattering-related component in the measured diffused optical signal;
    outputting to a connected display an image representative of the brain clot and a position and orientation of the probe;
    outputting to the connected display the identified composition of the brain clot; and
    outputting to the connected display a recommendation for selecting a brain clot removal technique using a method that matches the composition of the brain clot and includes removal of the brain clot via the working channel.

11. The method according to claim 10, wherein the first location of the first optical diffuser is more distal than the second location of the second optical diffuser.

12. The method according to claim 10, wherein the first location of the first optical diffuser is more proximal than the second location of the second optical diffuser.

13. The method according to claim 10, and comprising eliminating the clot based on the identified composition.

14. The method according to claim 10, and comprising tracking the probe using radiopaque markers disposed on the probe.

* * * * *